United States Patent [19]
Gaskell

[11] 4,023,559
[45] May 17, 1977

[54] SAMPLING CATHETER DEVICE

[75] Inventor: John Anthony Gaskell, Box Hill, Australia

[73] Assignee: Smith & Nephew (Australia) Pty. Limited, Australia

[22] Filed: Jan. 22, 1976

[21] Appl. No.: 651,226

[30] Foreign Application Priority Data
Jan. 28, 1975   Australia .......................... 0376/75

[52] U.S. Cl. .............................. 128/2 W; 128/2B; 128/269; 128/348
[51] Int. Cl.² ................. A61M 25/00; A61B 10/00
[58] Field of Search .................. 128/240–241, 128/348–351, 345, 2 R, 2 B, 2 W, 269, 304

[56] References Cited
UNITED STATES PATENTS

| | | |
|---|---|---|
| 217,711 | 7/1879 | Shiland .......................... 128/349 R |
| 1,595,180 | 8/1926 | Fisher .............................. 128/240 |
| 3,037,496 | 6/1962 | Melges ............................ 128/2 W |
| 3,513,830 | 5/1970 | Kalayjian ........................ 128/2 W |
| 3,776,219 | 12/1973 | Brown ............................. 128/2 B |

Primary Examiner—Dalton L. Truluck
Attorney, Agent, or Firm—Buell, Blanko & Ziesenheim

[57] ABSTRACT

A sampling catheter comprises an outer tube of resilient material which has an open and a closed end. The closed end is shaped so as to permit unrestricted entry into a body through a channel thereof and has means associated therewith enabling the opening of the closed end and protrusion therethrough by an inner tube extending within the outer tube upon said inner tube being pushed against the closed end.

A sampling sway is provided within the inner tube for extension beyond the end of the inner tube after protrusion thereof through the closed end.

3 Claims, 2 Drawing Figures

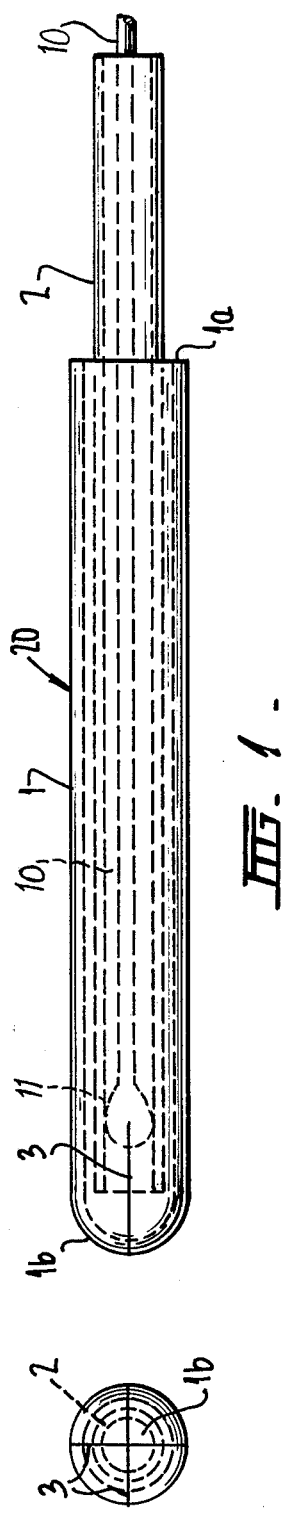
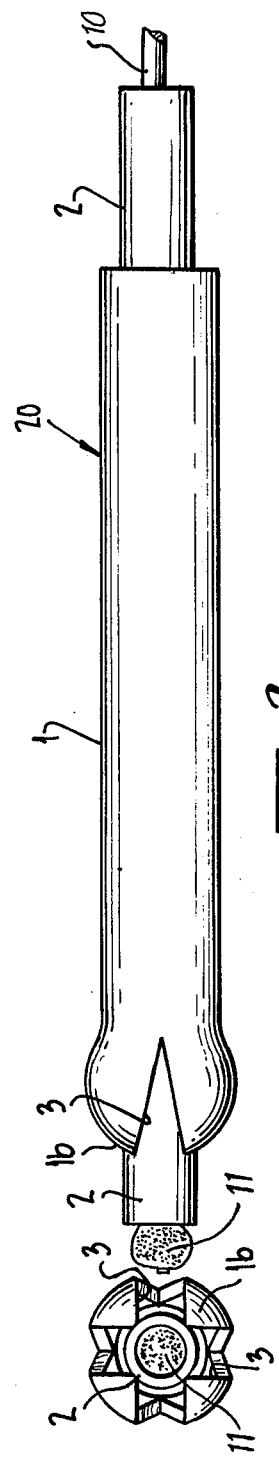

SAMPLING CATHETER DEVICE

This invention relates to catheter devices.

One of the disadvantages of prior art catheters, when used as a sampling device, is their disability to sufficiently protect the sample from contaminating matter which may be picked up as a result of the insertion and withdrawal of the device.

Accordingly, it is a principal object of the present invention to provide a catheter device which, when used as a sampling device, is adapted to prevent contamination of a selected sample from other matter during insertion and withdrawal of said device.

It is another object of the present invention to provide an improved catheter which may be used as an irrigator.

According to its broadest aspect, the invention provides a catheter comprising an outer tube of resilient material having an open and a closed end, said closed end being shaped so as to permit unrestricted entry into a body through a channel thereof and having means associated therewith enabling the opening of said closed end and protrusion therethrough by an inner tube extending within said outer tube upon said inner tube being pushed against said closed end.

The closed end of the outer tube may conveniently by convexly rounded and may be provided with at least one diametrically extending incision to enable the closed end to be opened as described hereinabove. Conveniently, the convex closed end is provided with a pair of incisions extending diametrically and mutually at right angles to provide four segments which are resiliently displaceable by the inner tube. The length and number of these incisions will depend on the nature of the resilient material, for example, hardness thereof.

One application of the above catheter is as a sampling device, for instance for taking mucus samples from a required site within a body, for example the vagina.

In this application, the inner tube is used to guide a swab stick which may be attached to an appropriate rod or tube. In practice, the outer tube is easily inserted in the appropriate channel of the body by virtue of its convexly rounded closed end to the required depth. The inner tube, conveniently marked to indicate the length to which it has to be inserted to open the closed end of the outer tube and to protrude for a nominal distance, is then pushed through the outer tube to the mark. At that stage the swab stick is pushed through the inner tube to a previously determined mark which will allow the swab to protrode beyond the end of the inner tube to allow the obtaining of a sample from the required site.

The swab stick is then withdrawn to within the inner tube and the catheter can then be withdrawn from the body.

According to another application, the catheter may be used as an irrigator for a selected area within the body, for example, the bladder, in which case the inner tube carries the irrigating liquid and the space between the inner and outer tube is used to drain the liquid from the selected area.

The catheter may also be used to assist in clearing an obstruction in a selected area within the body in which case the tip in the open position is used as a scraping device and the lumen between the inner and outer tubes permitting drainage fed in through the lumen of the inner tube.

A practical embodiment of a catheter according to this invention will now be described with reference to the accompanying drawings, wherein:

FIG. 1 shows the catheter in the position in which it is inserted into the body;

FIG. 2 shows the catheter in the operative position used, for example, for taking a sample.

Referring to FIG. 1, a catheter generally indicated as 20 consists of an outer tube 1 of resilient material having an open end 1a and a closed end 1b. The outer tube 1 holds an inner tube 2 which, when pushed against the closed end 1b of the outer tube 1 will pass through said closed end by virtue of a number of slits 3 provided in the closed end 1b of the resilient outer tube (vide FIG. 2). When the inner tube is retracted, the slitted end of the outer tube will again close.

A flexible swab stick 10 carrying a swab 11 on the end thereof is passed through the lumen of inner tube 2 and when tube 2 is projected through the closed end of tube 1 as shown in FIG. 2, the swab 11 may be pushed out of the end of tube 2 into the body cavity for collecting a sample from the body cavity. When the sample is collected the swab 11 is withdrawn into tube 2 and tube 2 is withdrawn into outer tube 1 so that the closed end seals the outer tube and the swab sample from contamination on withdrawal.

It will be appreciated that the relative hardness of the materials of the inner and outer tubes must be such that the inner tube will be capable of opening the closed end by the exertion of a small amount of axial pressure.

We claim:

1. A catheter sampling device comprising an outer tube of resilient material having an open and a normally closed end, said normally closed end being shaped so as to permit unrestricted entry into a body through a channel thereof and having means associated therewith enabling the opening of said normally closed end and protrusion therethrough by an inner tube extending within said outer tube upon said inner tube being pushed against said normally closed end and a flexible elongated member moving within said inner tube having sample collecting means at the end thereof designed to enter the body beyond said inner tube, said normally closed end being reclosable upon retraction of said inner tube and elongated member back within the confines of said outer tube.

2. A catheter as claimed in claim 1 wherein the closed end of the outer tube is convexly rounded and is provided with at least one diametrically extending incision.

3. A catheter as claimed in claim 2 wherein said closed end is provided with a pair of incisions extending diametrically and mutually at right angles.

* * * * *